Figure 3:
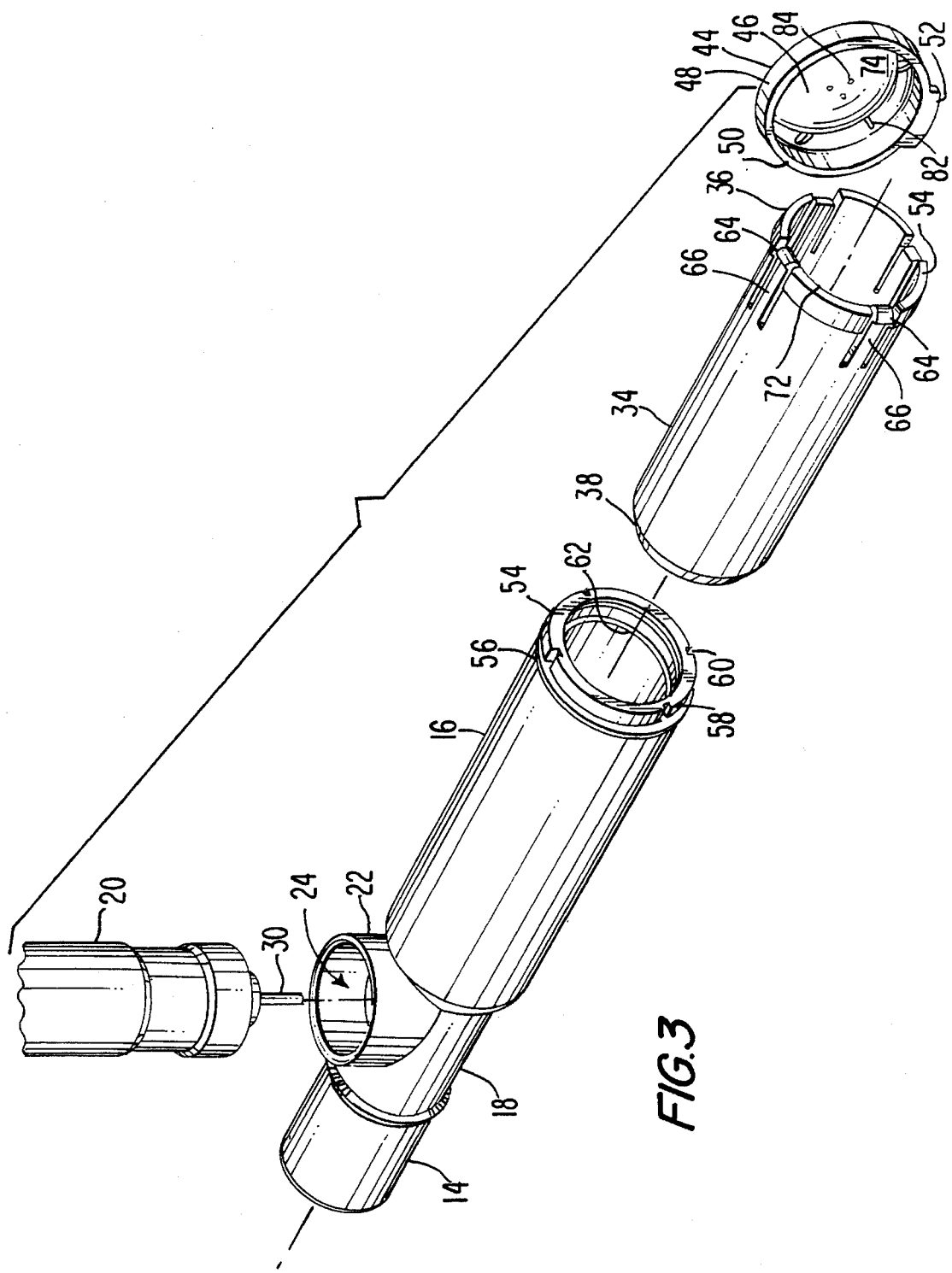

United States Patent [19]

Larson et al.

[11] Patent Number: 5,598,836
[45] Date of Patent: Feb. 4, 1997

[54] METERED DOSE INHALATION UNIT WITH SLIDE MEANS

[75] Inventors: Douglas A. Larson, River Forest; Thomas J. Danowski, Elgin, both of Ill.

[73] Assignee: Healthscan Products, Inc., Cedar Grove, N.J.

[21] Appl. No.: 452,139

[22] Filed: May 26, 1995

[51] Int. Cl.$^6$ ............................................. A61M 11/00
[52] U.S. Cl. ................................ 128/200.23; 128/200.14
[58] Field of Search ........................ 128/200.23, 200.14, 128/203.25; 222/522

[56] References Cited

U.S. PATENT DOCUMENTS

| | | |
|---|---|---|
| 3,184,115 | 5/1965 | Meshberg. |
| 3,456,644 | 7/1969 | Thiel .................... 128/200.23 |
| 3,789,843 | 2/1974 | Armstrong et al. .................... 180/54.1 |
| 3,809,294 | 5/1974 | Torgeson ............................ 128/203.15 |
| 3,897,779 | 8/1975 | Hansen ................................ 128/203.15 |
| 3,994,421 | 11/1976 | Hansen ................................ 128/200.23 |
| 4,292,966 | 10/1981 | Mono et al. ........................ 128/200.23 |
| 4,534,343 | 8/1985 | Nowacki et al. .................... 128/200.23 |
| 4,592,348 | 6/1986 | Waters, IV et al. .............. 128/200.23 |
| 4,852,561 | 8/1989 | Sperry ................................ 128/200.23 |
| 5,040,527 | 8/1991 | Larson et al. ...................... 128/200.23 |
| 5,297,542 | 3/1994 | Bacon ................................ 128/200.23 |
| 5,297,543 | 3/1994 | Larson et al. ...................... 128/200.23 |
| 5,318,016 | 6/1994 | Mecikalski ........................ 128/200.23 |
| 5,427,089 | 6/1995 | Kraemer ............................. 128/200.23 |

Primary Examiner—Edgar S. Burr
Assistant Examiner—Daniel J. Colilla
Attorney, Agent, or Firm—Schweitzer Cornman & Gross

[57] ABSTRACT

A spray-entrapped product such as dispensed by an MDI device includes an elongated passageway having a mouthpiece portion and a main chamber portion. The MDI device is mounted to direct a medication spray into the main chamber. A first air inlet allows a low-level inspiratory breath to be developed through the unit prior to operation of the MDI device. When the MDI device is operated a second, air inlet is opened, allowing a higher-level breath to be developed, which causes a high level of mixing with the MDI spray for efficient draws into the lungs. The second air inlet remains open after MDI operation ceases, insuring that a complete, high flow rate breath can be made to fully sweep the medication out of the chamber.

6 Claims, 4 Drawing Sheets

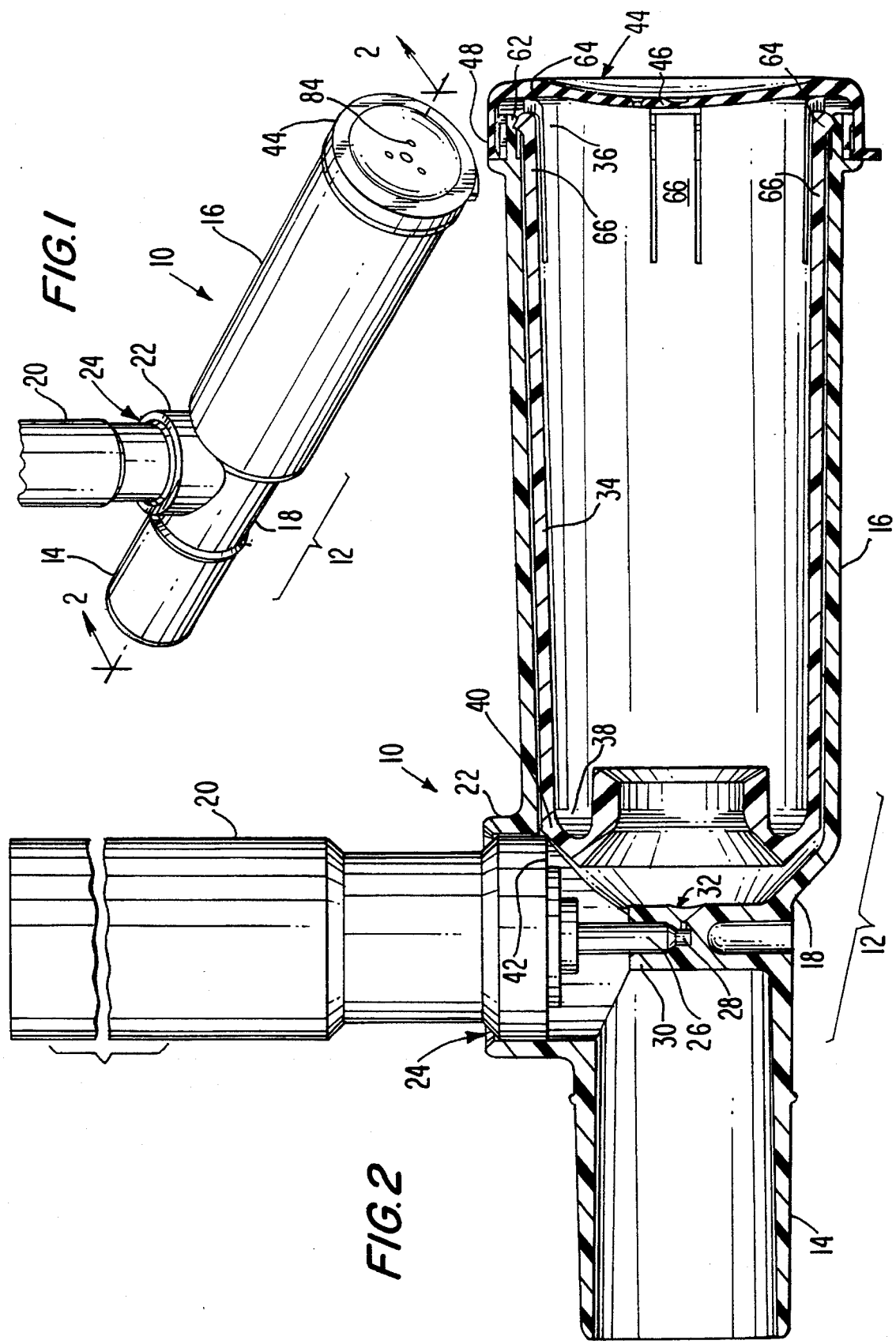

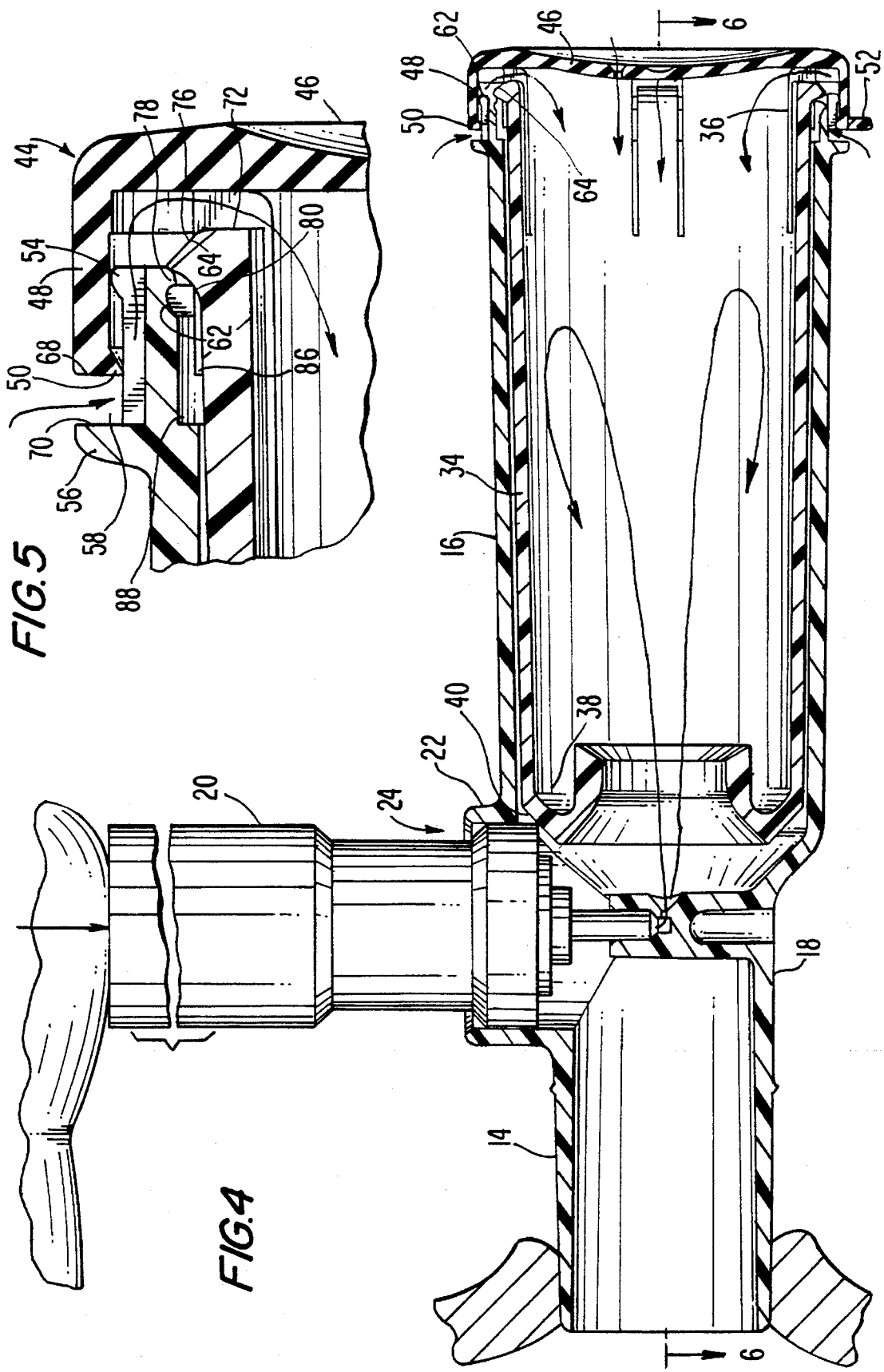

METERED DOSE INHALATION UNIT WITH SLIDE MEANS

BACKGROUND OF THE INVENTION

The use of a metered dose inhalation (MDI) apparatus for administering medicaments into the lungs of a patient is well known. In order to effectively channel the medication from the MDI canister to the mouth and subsequently into the lungs of the user, a variety of devices, generically known as "spacers", have been developed to accept an MDI canister dispenser and condition its output for entry into the lungs.

A preferred form of such a spacer, which provides a dynamic mixing chamber for the medication, is that illustrated and claimed in U.S. Pat. No. 5,040,527 to the present inventors. That patent discloses and claims a spacer in which the MDI output as directed away from the mouthpiece of the device. A first, low-level air flow is developed by the user's inspiratory breath through the spacer, in a direction opposed to the release of the medication, through a first air inlet. Simultaneous with the activation of the MDI dispenser and release of the medication spray, the opposed inspiratory air flow is increased by the opening at a second air inlet. The increased flow contacts the spray plume to cause a high level of mixing and a decrease in spray particle size, resulting in an efficient draw of the spray medication into the lungs of the user.

In the disclosed embodiment the duration of the increased air flow, which draws the medication into the lungs, is dependent upon the length of time which the MDI dispenser is depressed. Although the MDI dispenser releases a metered amount of spray independently of the depression time, depression of the dispenser maintains the opening of the second air inlet and thus the time during which increased air flow can be maintained. In certain cases, particularly with users having insufficient hand strength or dexterity, the MDI dispenser may not be able to be held down for a sufficient period, resulting in premature closing of the second air inlet and thus reducing the amount of the medication dose swept from the spacer volume.

It is accordingly a purpose of the present invention to provide a spacer apparatus which allows the onset of increased air flow to coincide with actuation of the MDI dispenser, but allows the flow to continue irrespective of continued actuation of the dispenser after the medication is dispensed.

Another purpose of the present invention is to provide a spacer of the aforementioned type in which increased airflow is generated by the opening of air inlet ports, the ports remaining open and exposed after actuation of the MDI dispenser.

Yet a further purpose of the present invention is to provide an MDI spacer which does not rely on a continuing manually applied force to control the duration of the increased air flow.

Still another purpose of the present invention is to provide a MDI spacer which generates a timed increased airflow which can be easily reset for a subsequent use, and which is economical and efficient to manufacture and use.

BRIEF DESCRIPTION OF THE INVENTION

In accordance with the foregoing and other features and benefits, the present invention utilizes an elongated chamber divided into a mouthpiece section and a main chamber section in the manner set forth in the '527 patent, the disclosure of which is incorporated herein by reference. The distal end of the main chamber is provided with a cap having a first set of apertures. In the unactuated state the cap seals the distal end of the chamber, and allows a first, low level inspiratory flow to be generated through the chamber by allowing ambient air to be drawn into the chamber through the first set of apertures.

A transverse aperture is provided in the chamber, between the mouthpiece and main chamber portions, and accepts a MDI dispenser, the nozzle of which engages a passageway which directs a spray of medication into the main chamber, away from the mouthpiece, when the MDI dispenser is operated. The downward motion of the dispenser during spray release simultaneously engages an actuator, which is coupled to the cap, and which displaces the cap from the end of the chamber, exposing a second set of apertures which permit an increased flow of ambient air into the chamber to be generated. The cap remains in the displaced position, even when the operating force on the MDI dispenser is removed, allowing the increased flow to continue for so long as the user continues with her inspiratory breath. When the breath is completed the cap is manually returned to the initial, sealing position, which resets the actuator for a subsequent use.

BRIEF DESCRIPTION OF THE DRAWINGS

A fuller understanding of the present invention and the features and benefits thereof will be achieved upon consideration of the following detailed description of a preferred, but nonetheless illustrative, embodiment thereof when reviewed in conjunction with the annexed drawings, wherein:

FIG. 1 is a perspective view of the invention with an MDI dispenser mounted thereon;

FIG. 2 is a side elevation view of the invention, the lower portion of which is shown in section taken along line 2—2 of FIG. 1;

FIG. 3 is an exploded perspective view of the embodiment;

FIG. 4 is a side elevation view, in section, taken along line 2—2 of FIG. 1, depicting the embodiment upon actuation;

FIG. 5 is a detailed view of the exposure of the second set of apertures as depicted in FIG. 4:

FIG. 6 is a top plan view, in section, taken along line 6—6 of FIG. 4;

FIG. 7 is an end elevation view, in section, taken along line 7—7 of FIG. 6; and FIG. 8 is a partial end elevation view, in action, taken along line 8—8 of FIG. 6, detailing the operation of the second apertures.

DETAILED DESCRIPTION OF A PREFERRED EMBODIMENT

Referring to FIGS. 1 and 2, spacer unit 10 comprises a body in the form of elongated, generally tubular member 12 having a mouthpiece section 14 and a main chamber portion 16, connected by an intermediate portion 18 which supports MDI dispenser 20. The dispenser is supported by a lip or collar 22 formed in the intermediate portion 18, which collar surrounds an accepting bore 24 for the nozzle end of the dispenser. The nozzle 26 of the dispenser is received within the vertical portion of right-angle bore 28 formed in internal pedestal 30. The horizontal portion of the right angle bore 28 terminates in a flared portion 32, causing the MDI medication to be sprayed into the main chamber portion 16 when downward pressure on the dispenser activates its internal valve.

Located within the main chamber portion 16 is tubular slide element 34, whose exterior diameter is chosen to provide a sliding fit within the main chamber portion. The slide element terminates at a first lipped end 36 and a second end 38 having an integral nozzle through which the contents of the main chamber portion 16 may be drawn to the mouthpiece and through which the flared portion 32 of the right angle bore 28 expels the medication from the MDI dispenser into the main chamber portion. The second end also is formed with an angled wall portion 40 against which the lower edge 42 of the MDI dispenser rests. The angle between the wall 40 and the horizontally-extending portion of the slide is preferably about 135°. It is to be appreciated that downward force upon the MDI dispenser produces a camming action against the angled wall, causing the slide element 34 to move to the right as shown in FIGS. 2 and 4, simultaneously with the activation of the MDI dispenser nozzle.

The distal end of the main chamber 16 is provided with cap 44, which mounts upon the end of the main chamber 16 and is adapted to move horizontally between first and second positions wherein, in the first position, a relatively airtight seal is created between the cap and main chamber and whereby, in the second position, a secondary series of airways into the main chamber interior are exposed.

In particular, and with particular reference to FIGS. 3 and 5, the cap 44 includes cover plate portion 46 having a plurality of airway bores 84 therethrough, which airway bores define a first air passageway and permit an initial airflow to enter the main chamber 16 when the user develops an inspiratory flow through the mouthpiece portion. The airway bores may be, for example, three in number with a diameter of 0.037 inches. The cap cover plate portion 46 is surrounded by a peripheral shoulder 48, which terminates inwardly directed lip 50. A tab 52 may be provided to assist in removing the cap from the main chamber portion.

Figure 8:
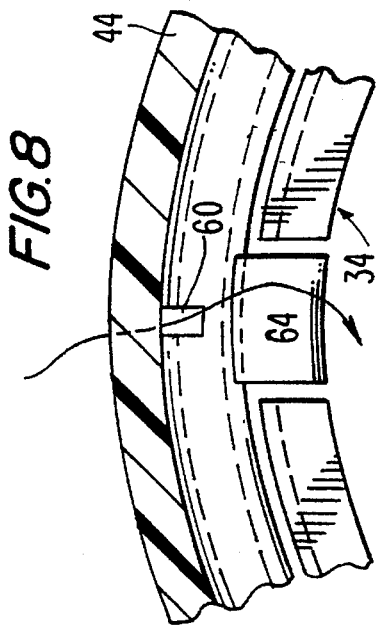
Figure 7:
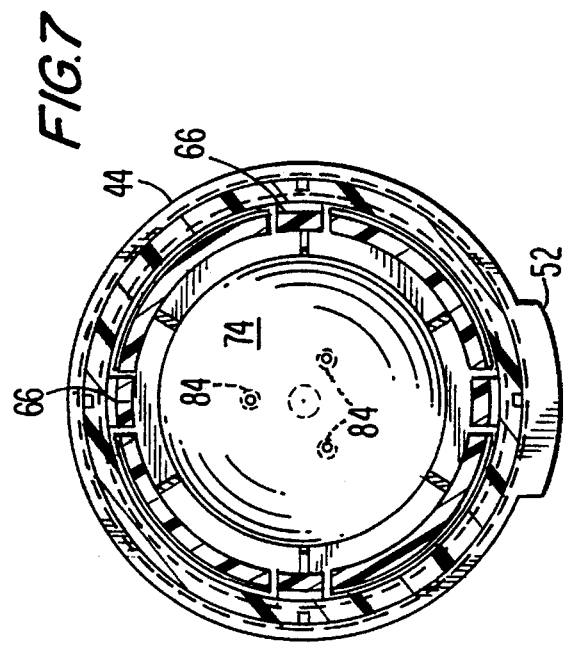

The second end of the main chamber 16, upon which the cap is placed, and perhaps best seen in FIG. 5, includes a pair of radial shoulders 54 and 56. The first shoulder 54 is at the end of the chamber portion, while the second shoulder 56 is located inwardly thereof. The two shoulders define an exterior radial groove 58 therebetween. The peripheral shoulder 48 of the cap is dimensioned to ride on shoulder 54, which may have a curved profile, the cap's inward peripheral lip 50 being retained within the groove 58, and preventing the cap from being removed from the main chamber end during normal use. As may be seen in FIGS. 3, 5 and 8, both shoulder 54 and the floor of groove 58 are provided with a series of notches 60, which define the secondary air passageways into the interior of the chamber.

The distal end of the tubular slide element 34 is provided with a plurality of integral outwardly projecting hook members 64, preferably four in number, which in turn are formed as the free end of fingers 66, best seen in FIGS. 3 and 4, formed as part of the slide element in a manner which provides radial flexibility to the hook members. In the initial operating position, depicted in FIG. 2, the hooks 64 engage an inner peripheral groove 62 in the main chamber portion 16, positioning and aligning the slide element with respect to the device body such that the slide's angular wall 40 is positioned for contact by the lower edge 42 of the MDI dispenser 20. To prevent the insertion of the slide beyond the engagement point, the slide includes an exterior shoulder 86, which abuts against wall 88 in the main chamber portion when the hooks engage the groove 62. With the slide so positioned the cap 44 can fully overlie the end of the main chamber portion 16, inward peripheral lip 50 of the cap being located at the left end of the groove 58, the end wall 68 of the cap contacting the wall 70 of shoulder 56 and forming a closure seal therebetween and for the second air passageways formed by the notches 60.

When the MDI dispenser 20 is depressed, creating a camming action with the inclined wall 40 of the slide element, the slide element moves to the right as presented in the figures, causing the hook members 64 to disengage from the complimentary inner peripheral groove 62 in the main chamber portion. The end 72 of the slide element, which is preferably dimensioned to abut the cap when the slide is in the initial starting position, contacts the inner surface 74 of cap cover plate portion 46, and thus drives the cap to the right, as shown in FIGS. 4 and 5. This action displaces the end wall surface 68 of the cap from the wall 70 of the chamber shoulder 56, exposing the slots 60, and creating a second passageway for air to enter the main chamber portion.

The inner peripheral groove 62 in the main chamber portion, with which the hooks 64 of slide fingers 66 engage, is provided with a right side cam surface of approximately 43° which is chosen to ensure that the fingers can be reset into the groove, to properly position the slide which will not require an excessive force to be applied to the slide to cam the fingers out of the groove during operation. The corresponding cam angle on the fingers, measured from the vertical to the camming surface 76, is approximately 47°. To permit the cap to be manually returned to its original position after operation the end of the main chamber portion of the housing is provided with a curved inner surface 78, beyond which the fingers pass during slide movement. That surface forms a camming surface of approximately 70° to engage the corresponding second camming surfaces 80 on the fingers, having an angle of approximately 20° from the vertical, when the cover is manually forced to the left, whereby the fingers cam back over the end surface of the main body portion to reset the slide member in its initial position with the fingers engaging the inner groove 62.

The choice of cam angles for the end of the main body portion the second slide camming surface and portion of the fingers result in a slide reset force of approximately 5 times that needed to move the slide during actuation. This differential further ensures that the cap cannot be drawn to the left by the inspiratory flow during use which would result in closure of the secondary airways. Because the cap is driven by contact between the end of the slide and the inner cap surface, the inner cap surface is provided with a series of ribs 82, best seen in FIGS. 3 and 5, which establishes an offset between the end of the slide and the cap, creating an airway into the slide and housing interior.

To operate the spacer unit, an MDI dispenser, which may be conveniently stored within the slide in the main body portion of the spacer, is installed upon the spacer in collar 22. The slide is positioned within the main body portion whereby the hook members 64 engage the inner groove 62 in the main chamber portion, positioning the slide for engagement with the dispenser and allowing the cap to be placed on the end of the spacer and oriented at its left-most position whereby its end wall 68 contacts the chamber shoulder wall 70, sealing the notches 60. Both slide and cap positioning can be preferably accomplished simultaneously sliding the cap to the left, as contact between the inner face of the cap and the end of the slide will return the slide to the start position.

With the unit prepared, the user places the end of the mouth piece section 14 in her mouth and starts an inspiratory breath, creating an initial, low level flow through the unit, ambient air being drawn in through the airway bores 84 forming a first air passageway in the end cap 84. Once the flow is created the MDI dispenser is depressed with respect to the spacer unit, actuating the MDI's internal valve and causing the medication spray to enter the main chamber 16.

Figure 6:
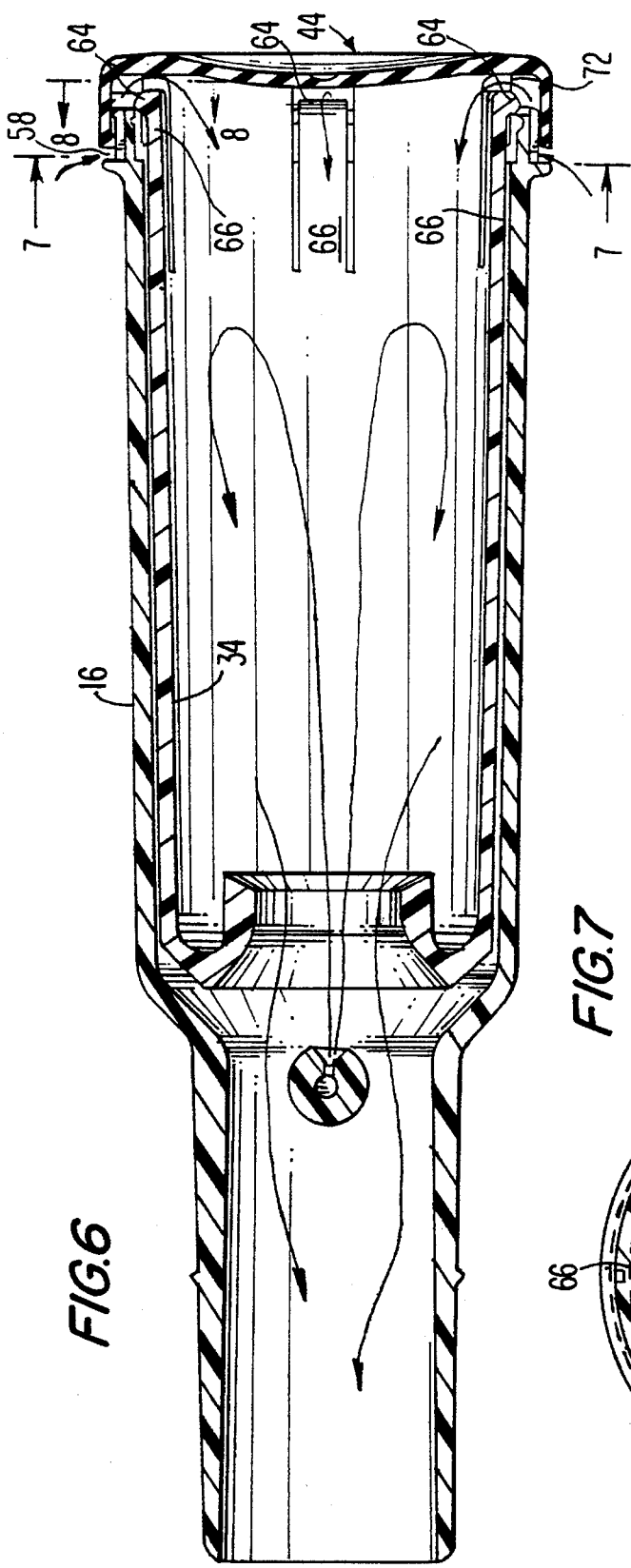

Simultaneously with the depression, the bottom edge 42 of the dispenser cams the slide to the right, as shown in FIG. 6, the slide fingers 66 leaving the main chamber portion groove 62. The slide drives the cap to the right, displacing the cap end wall 68 from the chamber shoulder wall 70 and exposing the notches 60. The notches 60 form a second air passageway between the interior of the main chamber portion and the ambient atmosphere, allowing an increased inspiratory flow to be developed. This increased flow engages the MDI spray in the main chamber, mixing with the spray and carrying the spray particles deep into the lungs. As the slide fingers pass beyond the end of the main chamber during actuation, the slide and thus the cap are maintained in the second, activated position against any suction effects created by the inspiratory flow, even when the user releases the MDI dispenser and thus terminates the camming action of the dispenser against the slide. The increased inspiratory flow thus can be maintained for the duration of the breath, insuring that the medication is fully and completely drawn into the lungs. The cross-sectional area of the notches 60 restrict the maximum inspiratory flow to approximately 60 liters/minute for a typical inspiratory breath.

We claim:

1. A spacer for an MDI dispenser, comprising a housing having a mouthpiece portion coupled to a main chamber portion, said main chamber portion having a sidewall and an open end; a slide element, and a cover positionable relative to said slide element having a first air passageway therethrough and a peripheral side wall, said cover being mounted upon said open end; second air passageway means upon said main chamber portion comprising a plurality of notches thereon proximate said open end, said cover being movable between a first position wherein said second air passageway means is closed and a second position wherein said second air passageway means is open and coupled to said main chamber; means for mounting an MDI dispenser upon the housing, including means for directing a spray from the dispenser into said main chamber portion; said slide element being engageable with the MDI dispenser to drive said cover into said second position upon activation of the dispenser; and lock means for maintaining said cover in said second position after activation of the dispenser.

2. The spacer of claim 1, wherein said slide element comprises a cylinder located within said housing having a first end engageable with said MDI dispenser and a second end engageable with said cover.

3. The spacer of claim 2, wherein said cylinder includes means for releasably positioning said cylinder in an initial position for engagement with said MDI dispenser.

4. The spacer of claim 3, wherein said releasable positioning means comprises latch means engageable with said main chamber portion.

5. The spacer of claim 4, wherein said latch means are located at said cylinder second end and said main chamber portion includes an internal peripheral groove, said latch means being positioned to engage said groove.

6. The spacer of claim 4, wherein said latch means comprise at least one latch finger.

* * * * *